United States Patent [19]

Jacklich

[11] Patent Number: 4,674,979

[45] Date of Patent: Jun. 23, 1987

[54] ENDODONTIC FILE

[76] Inventor: John J. Jacklich, 102 Western Ct., Santa Cruz, Calif. 95060

[21] Appl. No.: 800,206

[22] Filed: Nov. 21, 1985

[51] Int. Cl.4 .................... A61C 5/02

[52] U.S. Cl. .................... 433/102

[58] Field of Search .................... 433/102, 165, 166, 127

[56] References Cited

U.S. PATENT DOCUMENTS

| | | | |
|---|---|---|---|
| 3,924,334 | 12/1975 | Lentine et al. | 32/57 |
| 3,967,380 | 7/1976 | Malata et al. | 433/128 |
| 4,021,917 | 5/1977 | Nakanishi | 32/27 |
| 4,044,468 | 8/1977 | Kahn | 32/57 |
| 4,229,168 | 10/1980 | Scholz | 433/124 |
| 4,243,388 | 1/1981 | Arai | 433/27 |
| 4,260,379 | 4/1981 | Groves et al. | 433/102 |
| 4,295,827 | 10/1981 | Martin et al. | 433/81 |
| 4,299,571 | 11/1981 | McSpadden | 433/102 |
| 4,321,040 | 3/1982 | Miller et al. | 433/162 |
| 4,332,561 | 6/1982 | McSpadden | 433/102 |
| 4,478,578 | 10/1984 | Leonard | 433/165 |
| 4,484,891 | 11/1984 | Nash | 433/116 |
| 4,505,676 | 3/1985 | Gonser | 433/119 |

OTHER PUBLICATIONS

Osada Electric Co. "ENAC," undated, No. CN08504-30.

Medidenta International, Inc.; "Sonic Breakthrough," undated.

Caulk Endodontics; "Caulk Endoplus," 1985.

*Primary Examiner*—Robert Peshock

[57] ABSTRACT

An endodontic file is provided for use in root canal procedures. The file has an elongated blade with cutting edges formed on the lower portion thereof and having a shank at its upper portion. A file head is provided having a passageway formed therein which receives the shank of the blade. The end of the shank is flared to prevent the shank from being drawn through the passageway in one direction. By anchoring the file blade in this manner, the use of a low profile handpiece is facilitated for ease of use in a patient's mouth.

2 Claims, 3 Drawing Figures

44 80 65 70 64 61 60 62 43

ENDODONTIC FILE

CROSS-REFERENCE TO RELATED APPLICATIONS

This invention relates to an endodontic file which may be used in conjunction with the device described in my application entitled Improved Handpiece for Use in Root Canal Procedures filed simultaneously with this application.

BRIEF SUMMARY OF THE INVENTION

This invention relates generally to endodontic procedures such as root canal procedures. More particularly, this invention provides a file in which the upper shank of the file is anchored to a file head by flaring the tip of the shank of the blade, rather than by the use of cement as has been done with prior endodontic files.

The prior art method of cementing the file shaft to a file head requires sufficient surface area, which further requires a relatively long portion of the blade shank. This in turn results in a relatively high profile handpiece which must be inserted into the patient's mouth by the user. The present invention facilitates the use of a low profile handpiece which is much easier to use in the patient's mouth.

A primary object of this invention is to provide an endodontic file for use in root canal and related procedures in which the blade may be used in a low profile handpiece.

A further object of the invention is to provide an endodontic file in which the tip of the shank of the file blade is tapered and seats against a passageway in a file head so that the blade will not separate from the file head during operation.

A further object of the invention is to provide an endodontic file utilizing an elongated cylindrical blade in which the height of the file head is equal to or less than five times the diameter of the shank of the blade.

Other objects and advantages of the invention will become apparent from the following description of a preferred embodiment and the drawings wherein:

DETAILED DESCRIPTION OF THE DRAWINGS

Figure 2:
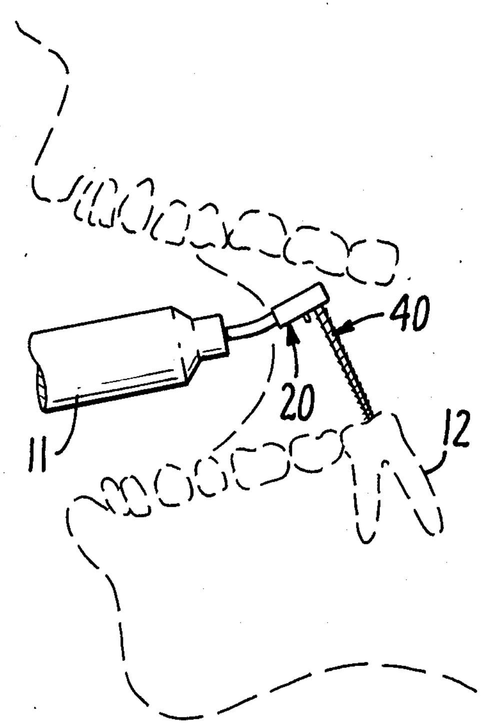
FIG. 2 is a perspective view of a route canal procedure using the endodontic file of this invention.

As shown in FIG. 2, a handpiece 11 is being used in a root canal procedure in tooth 12.

Adapter 20 connects to handpiece 11 and supports endodontic file 40 during the root canal procedure.

The present invention relates only to the configuration of the file 40. Adapter 20 and handpiece 11 may be constructed in accordance with my co-pending patent application entitled Improved Handpiece for Use in Root Canal Procedures filed simultaneously with this application. File 40 may also be used with other adapters and other handpieces.

Figure 1:
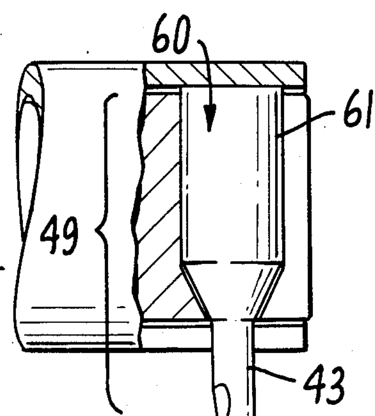
FIG. 1 is an elevational view, partly in section, of an endodontic file constructed in accordance with the invention.

FIG. 1 shows the details of the present invention. An elongated file blade 41 has cutting edges 42 formed on the lower portion 48 thereof and has a shank portion 43 at its upper portion 49.

File head means 60 has a generally cylindrical body 61 with a passageway 62 formed therein for receiving shank 43 of blade 41. Flare means 70 is formed at the end of shank 43 to prevent shank 43 from being drawn through passageway 62 in one direction. With respect to FIG. 3, flare means 70 prevents shank 43 from being drawn downwardly through passageway 62.

In operation, the cutting stroke of blade 41 occurs when file head means 60 exerts upward pressure on the file blade 41. In this mode, it is apparent that flare means 70 transmits the pulling force from file head means 60 to the shank 43 of file blade 41. The cutting stroke presents the largest force to be applied to the blade 41 and it is critical that the blade 41 does not become separated from the file head means 60 during the cutting stroke. Flare means 70 is very effective in preventing blade 41 from moving in the downward direction as shown in FIG. 2 relative to file head means 60.

Flare means 70 is a flattened portion 71 of shank 43. Flattened section 71 is formed by starting with cylindrical shank 43 and hammering or otherwise shaping the upper tip 44 in a direction perpendicular to the longitudinal axis of blade 41. For a shank of 1/32 inch diameter, the shaping by hammering is performed preferably on the last 1/32 inch or more of the shank 43. This shaping procedure produces an elliptical cross section of shank 43 near its end 44 and requires the pressing of flared or shaped shank 43 into passageway 62. The frictional force of the pressing resists upward motion of shank 43 relative to file head 60.

A recess 65 is formed in file head means 60 at the upper end 64 of passageway 62. Recess 65 receives flare means 70 and also receives cement 80 which provides additional bonding of flare means 70 and shank 43 to file head means 60. Cement 80 assists in preventing the upward motion of shank 43 relative to file head means 60. Cement 80 is color coded to indicate the size of blade 41.

Figure 3:
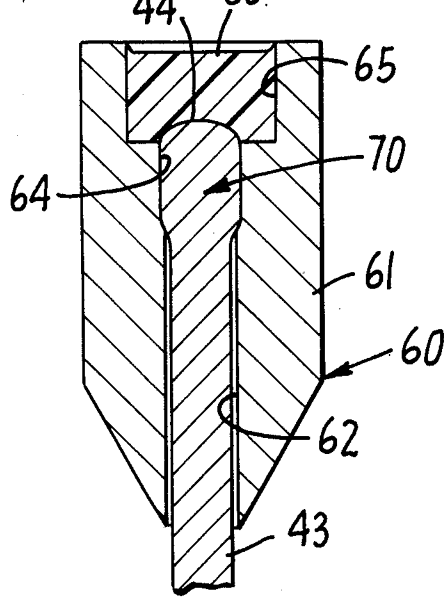
FIG. 3 is a sectional view of a portion of the file shown in FIG. 1.

In the embodiment shown in FIG. 3, shank 43 is cylindrical and is 1/32 of an inch in diameter and the vertical height of file head means 60 is 5/32 of an inch. Therefore, a relatively low profile handpiece adapter 20 may be used in conjunction with the file provided by this invention. The use of a low profile (i.e. minimum height) adapter which carries the file of this invention enables much easier use of the device in a patient's mouth, as shown in FIG. 2.

I have observed in practice that the blade 41 will break before flare means 70 will be drawn downwardly through passageway 62. I have also found that the vertical height of the file head means 60 should be equal to or less than five times the diameter of the shank 43 of blade 41.

What is claimed is:

1. An endodontic file for use in root canal procedures, comprising:

an elongated file blade having cutting edges formed on the lower portion thereof and having a cylindrical shank at its upper portion, file head means having a cylindrical passageway formed therein for receiving said shank, flare means formed at the end of said shank and comprising a flattened portion of said shank so that said shank must be pressed into said passageway, said flare means preventing said shank from being drawn through said passageway in one direction and the height of said file head is equal to or less than five times the diameter of said shank.

2. The apparatus of claim 1 further comprising a recess formed in said file head means at one end of said passageway for receiving said flare means and for receiving cement to bond said flare means to said file head means.

* * * * *